United States Patent [19]
Bonrath

[11] Patent Number: 5,900,494
[45] Date of Patent: * May 4, 1999

[54] METHOD OF MAKING D,L-α-TOCOPHEROL

[75] Inventor: Werner Bonrath, Freiburg, Germany

[73] Assignee: Roche Vitamins Inc., Parsippany, N.J.

[*] Notice: This patent issued on a continued prosecution application filed under 37 CFR 1.53(d), and is subject to the twenty year patent term provisions of 35 U.S.C. 154(a)(2).

[21] Appl. No.: 08/778,479

[22] Filed: Jan. 3, 1997

[30] Foreign Application Priority Data

Jan. 5, 1996 [CH] Switzerland ................ 31/96

[51] Int. Cl.$^6$ .................................................. C07D 311/72
[52] U.S. Cl. ............................................................ 549/411
[58] Field of Search .............................................. 549/411

[56] References Cited

U.S. PATENT DOCUMENTS

| | | | |
|---|---|---|---|
| 3,444,213 | 5/1969 | Nelan | 260/345.5 |
| 3,459,773 | 8/1969 | Moroe et al. | 260/345.5 |
| 3,708,505 | 1/1973 | Greenbaum et al. | 260/345.5 |
| 3,789,086 | 1/1974 | Frick et al. | 260/345.5 |
| 4,217,285 | 8/1980 | Yoshino et al. | 260/345.5 |
| 4,634,781 | 1/1987 | Finnan | 549/411 |

FOREIGN PATENT DOCUMENTS

| | | |
|---|---|---|
| 012 824 | 9/1980 | European Pat. Off. . |
| 960 720 | 3/1957 | Germany . |
| 1 015 446 | 9/1957 | Germany . |
| 24 04 621 | 8/1975 | Germany . |
| WO 88/02661 | 4/1988 | WIPO . |
| WO 95/19222 | 7/1995 | WIPO . |

OTHER PUBLICATIONS

Waller et al., "Catalysis with Nafion: What happens when you hang a sulfonic acid group on a perfluorinated membrane?", Chemtech, vol. 17, pp. 438–441 (Jul. 1987).
Chemical Abstract 103:104799d, 1985.
Chemical Abstract 103:123731s, 1985.
Chemical Abstract 110:39217, 1987.
Derwent Abstract No. 43517V/24, 1974.
Olah, George A. et al., Synthesis, pp. 513–531 (Jul. 1986).

*Primary Examiner*—Ba K. Trinh
*Attorney, Agent, or Firm*—George W. Johnston; Dennis P. Tramaloni

[57] ABSTRACT

A process for the manufacture of d,l-α-tocopherol by condensing trimethylhydroquinone with isophytol comprises carrying out the condensation in the presence of a polyperfluoroalkylenesulphonic acid as the catalyst and in a solvent, especially an aprotic solvent. The catalyst is preferably a polyperfluoroalkylenesulphonic acid from the Nafion® series, e.g., Nafion NR 50® or Nafion 117®.

15 Claims, No Drawings

METHOD OF MAKING D,L-α-TOCOPHEROL

Background of the Invention

The present invention is concerned with a novel process for the manufacture of d,l-α-tocopherol by condensing trimethyl-hydroquinone with isophytol. d,l-α-Tocopherol is a diastereomer mixture of a derivative of the vitamin E group.

Various processes for the manufacture of d,l-α-tocopherol by condensing trimethylhydroquinone with isophytol have already been described.

Thus, for example, according to Chem. Abstracts (C.A.) 103, 104799 (1985), C.A. 103, 123731 (1985) and C.A. 110, 39221 (1989) the condensation is carried out in the presence of zinc and zinc chloride ($ZnCl_2$) and a protonic acid such as a hydrohalic acid, e.g., hydrochloric acid (HCl), trichloroacetic acid, acetic acid and the like, especially $ZnCl_2$/HCl, as the catalyst.

The manufacture of d,l-α-tocopherol by reacting trimethylhydroquinone with phytyl chloride or isophytol in the presence of boron trifluoride ($BF_3$) or its etherate ($BF_3 \cdot Et_2O$) as the catalyst is described in German Offenlegungsschriften 960720 and 1015446 as well as in U.S. Pat. No. 4,634,781.

The condensation of trimethylhydroquinone with isophytol or phytol, which has been treated with ammonia or amines, in the presence of $ZnCl_2$/HCl or a Lewis acid/HCl, such as, e.g., $BF_3$ or aluminium trichloride ($AlCl_3$), as the catalyst is described in U.S. Pat. No. 4,634,781.

According to U.S. Pat. No. 3,789,086 the condensation is carried out in the presence of a $FeCl_2$/Fe/HCl catalyst, while according to EP-A 12824 the condensation is effected using trifluoroacetic acid.

All of these previously known processes have serious disadvantages: thus, corrosion problems occur in all processes, when boron trifluoride is used there are additionally toxicity problems with the boron trifluoride adducts, and when iron or zinc is used there is a contamination of the waste water with iron or zinc ions which today is no longer acceptable.

The use of ion exchangers, e.g., Amberlyst 15®, as the catalyst is described in U.S. Pat. No. 3 459 773. However, according to this process the d,l-α-tocopherol could not be obtained in the requisite purity.

SUMMARY OF THE INVENTION

The object of the present invention is to provide a process for the manufacture of d,l-α-tocopherol by condensing trimethyl-hydroquinone with isophytol in the presence of a catalyst which does not have the disadvantages of the previously known procedures. For this purpose, it is necessary that the catalyst employed does not have a corrosive action, is non-toxic, does not contaminate the environment and catalyzes the desired reaction as selectively as possible and in high yields. Furthermore, the catalyst should display its activity in truly only catalytic amounts and should be readily separable and re-usable several times.

In the scope of the present invention this object is achieved by carrying out the condensation of trimethylhydroquinone with isophytol in the presence of a polyperfluoroalkylenesulphonic acid and in a solvent.

DETAILED DESCRIPTION OF THE INVENTION

The invention comprises a process of making d,l-α-tocopherol by reacting trimethylhydroquinone and isophytol dispersed in an aprotic organic solvent in the presence of a polyperfluoroalkylenesulphonic acid whereby the trimethylhydroquinone and isophytol condense to produce the d,l-α-tocopherol.

The temperature at which the condensation reaction of the invention is carried out is not critical. Any temperature at which the reaction occurs may be used in accordance with the present invention. The condensation is preferably effected at temperatures between about 80° C. and 140° C., especially between about 85° C. and 120° C.

The ratio of the reactants used in the method of the present invention is not critical. Any ratio at which the condensation reaction occurs may be used in accordance with the present invention. Preferably, about equimolar amounts of the two educts trimethylhydroquinone and isophytol are used.

The preferred aprotic organic solvents used in accordance with the present invention are aliphatic and cyclic ketones, e.g., isobutyl methyl ketone and diethyl ketone and, respectively, cyclopentanone and isophorone; aliphatic and cyclic esters, e.g., ethyl acetate, isopropyl acetate and, respectively, γ-butyrolactone; and aromatic hydrocarbons, e.g., toluene and xylene. Polar aprotic solvents, e.g., diethyl ketone, ethyl acetate, isopropyl acetate and γ-butyrolactone, are especially preferred.

The amount of solvent used in carrying out the process of the invention is not critical so long as the amount is sufficient to provide for reaction mixture fluidity and prevent the reaction from becoming overly exothermic. Preferably, the amount of solvent used is from 200–1000 ml per mole of the reactant which is present in the largest amount.

The condensation reaction takes place according to the following Reaction Scheme:

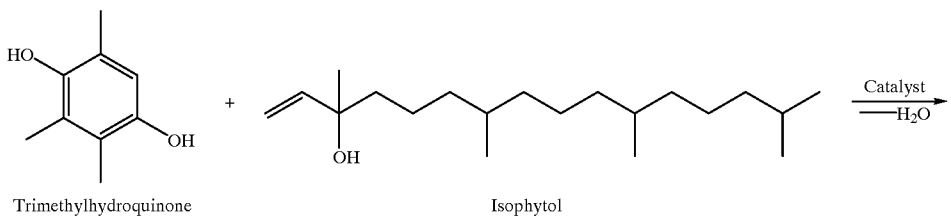

Trimethylhydroquinone            Isophytol

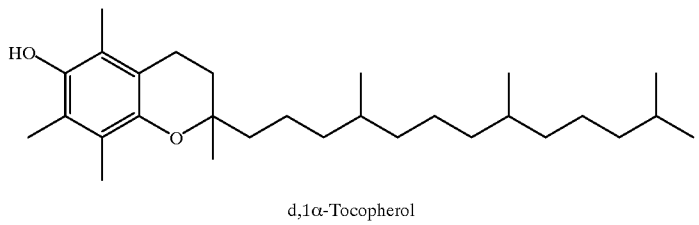

d,1α-Tocopherol

The polyperfluoroalkylenesulphonic acid used as the heterogenous catalyst is not critical. Any conventional polymeric perfluoroalkylenesulphonic acid which is insoluble in the solvent or the reactants may be used as the catalyst in accordance with the present invention. Polyperfluoroalkylenesulphonic acid catalysts are well known in the art, and are referred to as "superacid" catalysts because of their high acid strength. An example of such a catalyst is a compound of the formula:

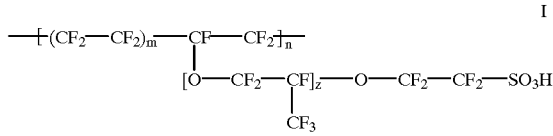

I wherein m, n and z are positive integers and m is varied depending upon the sulphonic acid content desired for the polymer, n is directly related to the molecular weight of the polymer, and z is typically 1–3, preferably 1. Such catalysts may be prepared by any conventional means known in the art. Such a polyperfluoroalkylenesulphonic acid catalyst is, however, sold by Du Pont under the trademark Nafion®.

Another example of a polyperfluoroalkylenesulphonic acid useful in accordance with the invention is a compound of the formula:

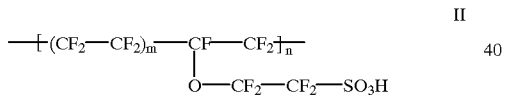

II wherein m and n are positive integers and m is varied depending upon the sulphonic acid content desired for the polymer and n is directly related to the molecular weight of the polymer. Such catalysts may be prepared by any conventional means known in the art.

The sulphonic acid content of catalysts useful in accordance with the present invention is not critical, so long as it is sufficient to catalyze the condensation of the reactants. Typically, polyperfluoroalkylenesulphonic acid catalysts have at least 5% sulphonic acid content. The physical form of the polyperfluoroalkylenesulphonic acid catalyst is not critical. Typically, the catalyst is available in the form of membranes (thin films) or beads. The membrane form should be preferably comminuted before use to provide a greater catalytic surface area. The bead form is, however, preferred since a comminution step is avoided. Those polyperfluoroalkylenesulphonic acids of formula 1, which are available under the proprietary name Nafion® (Du Pont, Wilmington, Del.), are preferably used as the acidic condensation catalysts in the process in accordance with the invention. Nafion® NR 50 (available in bead form) and Nafion® 117 (available only in membrane form) are especially preferred. The Nafion® NR 50 is most especially preferred.

Preferably, 1–20 wt. %, especially 1–10 wt. %, of catalyst is used based on the weight of the trimethylhydroquinone or isophytol used. Since a wide range of catalyst concentrations may be used, either the weight of the trimethylhydroquinone or the weight of the isophytol may be used as the basis for measuring the concentration of the catalyst.

The order in which the reactants are combined is not critical. Preferably, the isophytol is added dropwise to a suspension of the trimethylhydroquinone and the catalyst in the solvent. The rate at which the isophytol is added is not critical. Preferably, the isophytol is added dropwise over a period of 1–4 hours. After completion of the isophytol addition and an appropriate subsequent reaction period, the working up is effected by procedures conventionally used in organic chemistry. Conveniently, the reaction solution is separated from the heterogeneous catalyst by filtration or by decantation and the solvent is evaporated off.

The process of the invention enables the catalyst used to be separated readily and to be re-used several times.

The following Examples for the manufacture of d,l-α-tocopherol by condensing trimethylhydroquinone with isophytol illustrate advantageous embodiments of the process in accordance with the invention, but they are not intended to be limiting in any manner. All temperatures are given in degrees Celsius.

EXAMPLE 1

Condensation of Trimethylhydroquinone with Isophytol in Toluene 31.4 g (200 mmol) of trimethylhydroquinone and 8.5 g of the 30 polyperfluoroalkylenesulphonic acid catalyst (Nafion NR 50®) were suspended in 50 ml of toluene in a 500 ml four-necked flask at room temperature. The suspension was heated to 107°. 73 ml (200 mmol) of isophytol were added dropwise within 2 hours. The reaction mixture was heated to reflux for 30 minutes. After cooling to room temperature the catalyst was filtered off and the filtrate was concentrated on a rotary evaporator. The crude product obtained was analyzed by gas chromatography according to known procedures.

Yield: 75.33% of theory of d,l-α-tocopherol.

EXAMPLE 2

Condensation of Trimethylhydroquinone with Isophytol in Ethyl Acetate 31.4 g (200 mmol) of trimethyihydroquinone and 8.5 g of the polyperfluoroalkylenesulphonic acid catalyst (Nafion NR 50®) were suspended in 100 ml of ethyl acetate in a 500 ml four-necked flask at room temperature. The suspension was heated to 85°. 73 ml (200 mmol) of isophytol were added dropwise within 4 hours. The solvent was subsequently distilled off.

Yield: 83.55% of theory of d,l-α-tocopherol.

In a variant, 9.8 ml of Nafion 117® were used in place of Nafion NR 50®.

Yield: 63.49% of theory of d,l-(α-tocopherol.

EXAMPLE 3

Condensation of Trimethylhydroquinone with Isophytol in Diethyl Ketone 31.4 g (200 mmol) of trimethylhydroquinone and 15 g of the polyperfluoroalkylenesulphonic acid catalyst (Nafion NR 50®) were suspended in 50 ml of diethyl ketone in a 500 ml four-necked flask at room temperature. The suspension was heated to 109°. 73 ml (200 mmol) of isophytol were added dropwise within 2 hours. The reaction mixture was heated to reflux for 30 minutes. After cooling to room temperature the catalyst was filtered off and the filtrate was concentrated on a rotary evaporator.

Yield: 84.69% of theory of d,l-α-tocopherol.

EXAMPLE 4

Condensation of Trimethylhydroquinone with Isophytol in γ-Butyrolactone 31.4 g (200 mmol) of trimethylhydroquinone and 8.5 g of the polyperfluoroalkylenesulphonic acid catalyst (Nafion NR 50®) were suspended in 50 ml of γ-butyrolactone in a 500 ml four-necked flask at room temperature. The suspension was heated to 117°. 73 ml (200 mmol) of isophytol were added dropwise within 2 hours. The reaction mixture was heated to reflux for 30 minutes. After cooling to room temperature the catalyst was filtered off and the filtrate was concentrated on a rotary evaporator.

Yield: 84.5% of theory of d,l-α-tocopherol.

I claim:

1. A process for making d,l-α-tocopherol which comprises reacting trimethylhydroquinone and isophytol dispersed in an aliphatic ketone or cycle ester solvent in the presence of a polyperfluoroalkylenesulphonic acid catalyst whereby the trimethylhydroquinone and isophytol condense to produce the d,l-α-tocopherol.

2. The process of claim 1 wherein the catalyst is a compound of the formula:

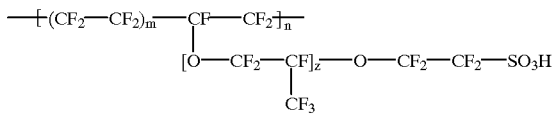

wherein m and n are positive integers, z is 1–3, and the value of m results in the sulphonic acid content of the catalyst being at least 5%.

3. The process of claim 2 wherein z is 1.

4. The process of claim 2 wherein the catalyst is Nafion® NR 50 or Nafion® 117.

5. The process of claim 4 wherein the catalyst is present in an amount from about 1% to about 20% by weight of the trimethylhydroquinone or the isophytol.

6. The process of claim 5 wherein the catalyst is present in an amount from about 1% to about 10% by weight of the trimethylhydroquinone or the isophytol.

7. The process of claim 6 wherein the reaction is carried out at a temperature in the range from about 80° C. to about 140° C.

8. The process of claim 7 wherein the reaction is carried out at a temperature in the range from about 85° C. to about 120° C.

9. The process of claim 6 wherein the solvent is isobutyl methyl ketone, diethyl ketone, or γ-butyrolactone.

10. The process of claim 1 wherein the catalyst is a compound of the formula:

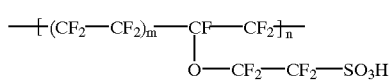

wherein m and n are positive integers and the value of m results in the sulphonic acid content of the catalyst being at least 5%.

11. The process of claim 10 wherein the catalyst is present in an amount from about 1% to about 20% by weight of the trimethylhydroquinone or the isophytol.

12. The process of claim 11 wherein the catalyst is present in an amount from about 1% to about 10% by weight of the trimethylhydroquinone or the isophytol.

13. The process of claim 12 wherein the reaction is carried out at a temperature in the range from about 80° C. to about 140° C.

14. The process of claim 13 wherein the reaction is carried out at a temperature in the range from about 85° C. to about 120° C.

15. The process of claim 12 wherein the solvent is isobutyl methyl ketone, diethyl ketone, or γ-butyrolactone.

* * * * *